(12) United States Patent
Sambasivam et al.

(10) Patent No.: US 6,573,392 B1
(45) Date of Patent: Jun. 3, 2003

(54) PROCESS FOR MANUFACTURING SIMVASTATIN AND THE NOVEL INTERMEDIATES

(75) Inventors: Ganesh Sambasivam, Bangalore (IN); Madhavan Sridharan, Bangalore (IN); Poornaprajna Acharya, Bangalore (IN); Joy Mathew, Bangalore (IN)

(73) Assignee: Biocon India Limited, Bangalore District (IN)

( * ) Notice: Subject to any disclaimer, the term of this patent is extended or adjusted under 35 U.S.C. 154(b) by 0 days.

(21) Appl. No.: 10/129,861

(22) PCT Filed: Nov. 11, 1999

(86) PCT No.: PCT/IN99/00063

§ 371 (c)(1),
(2), (4) Date: May 10, 2002

(87) PCT Pub. No.: WO01/34590

PCT Pub. Date: May 17, 2001

(51) Int. Cl.$^7$ .............................................. C07D 309/30
(52) U.S. Cl. .................................................... 549/292
(58) Field of Search ......................................... 549/292

(56) References Cited

U.S. PATENT DOCUMENTS

| | | | |
|---|---|---|---|
| 4,820,850 A | 4/1989 | Verhoeven et al. | 549/292 |
| 5,223,415 A | 6/1993 | Conder et al. | 435/125 |
| 5,393,893 A | 2/1995 | Kubela et al. | 549/292 |
| 5,763,646 A | 6/1998 | Kumar et al. | 560/252 |
| 5,763,653 A | 6/1998 | Khanna et al. | 560/252 |
| 5,917,058 A | 6/1999 | Kumar et al. | 549/292 |
| 5,939,564 A | 8/1999 | Kumar et al. | 549/292 |
| 6,252,091 B1 | 6/2001 | Zupancic et al. | 549/292 |
| 6,271,398 B1 | 8/2001 | Van Dalen et al. | 549/292 |
| 6,294,680 B1 | 9/2001 | Vries et al. | 549/373 |
| 6,307,066 B1 | 10/2001 | Murthy et al. | 549/292 |
| 6,331,641 B1 | 12/2001 | Taoka et al. | 549/292 |

FOREIGN PATENT DOCUMENTS

| | | |
|---|---|---|
| EP | 0 864 560 | 9/1998 |
| EP | 0 864 569 | 9/1998 |
| EP | 0 940 395 | 9/1999 |
| EP | 0 955 297 | 11/1999 |
| WO | WO 98/32751 | 7/1998 |
| WO | WO 99/11258 | 3/1999 |

*Primary Examiner*—Taofiq Solola
(74) *Attorney, Agent, or Firm*—Choate, Hall & Stewart; Sam Pasternak

(57) ABSTRACT

This invention describes the synthesis of simvastatin from lovastatin by converting the lovastatin to lova amide using a secondary amine and subsequent reaction with a metal amide base generated from n-butyl lithium and pyrrolidine and followed by treatment with methyl iodide to give desired C-methylated intermediate. This intermediate was further transformed to the final product, simvastatin. This method of production consumes lesser quantities of metal amide, gives fewer side reactions and a lowered overall cost of manufacture of simvastatin than other procedures reported.

11 Claims, No Drawings

PROCESS FOR MANUFACTURING SIMVASTATIN AND THE NOVEL INTERMEDIATES

This Application is a 371 of PCT/IN99/00 filed Nov. 11, 1999.

BACKGROUND

The naturally occurring compounds of formula I and their semi-synthetic analogs are very active antihypercholesterolemic agents that function by limiting the cholesterol biosynthesis by inhibiting the HMG-CoA reductase enzyme.

Compounds of formula Ia, shown in page 9, include the natural fermentation products like mevinolin (disclosed in U.S. Pat No. 4,231,938 and also known as lovastatin), compactin (disclosed in U.S. Pat No. 3,983,240) and a variety of semi-synthetic and totally synthetic analogs thereof, all having the natural 2-methylbutyrate side chain.

Compounds of formula IIa, shown in page 9, having a 2,2-dimethylbutyrate side chain (e.g., simvastatin) are known to be more active inhibitors of HMG-CoA reductase than their 2-methylbutyate analogs and thus of greater utility in the treatment of artherosclerosis, hyperlipemia, familial hypercholesterolemia and similar disorders.

It has been proved that products having a 2,2-dimethylbutryate side chain are more active inhibitors than their analogs. The introduction of simvastatin (IIa) into the market as a more potent HMG-CoA reductase inhibitor than lovastatin (Ia) has provided a need for a high yielding process which is more economically efficient and environmentally sound than those disclosed in the prior art.

Compounds of formula Ia (e.g. simvastatin) with the 2,2-dimethylbutyrate side chain and processes for their preparation are disclosed in U.S. Pat No. 4,444,784 and EPO patent specification No. 33538. The route described are both tedious and cumbersome and gives very poor over all yields.

Simvastatin has also been prepared by the α-alkylation of the ester moiety as described in U.S. Pat. Nos. 4,582,915 and 4,820,850.

U.S. Pat. No. 4,582,915 discloses the direct methylation in a single step using a metal alkyl and a methyl halide. The process suffers from poor conversion coupled with many side reactions which complicate both isolation and purification of the final product, simvastatin.

The U.S. Pat. No. 4,820,850 describes a good conversion to simvastatin using a single charge of the amide base and alkyl halide. However, the process suffers from a large number of steps and hence affecting the over all yield. Further, the process utilizes a highly expensive silylating agent to protect the hydroxyl groups thus rendering the route cost ineffective.

Recent patents like U.S. Pat. Nos. 5,763,653 and 5,763,646 describes the synthesis of the simvastatin from mevinolinic acid or the salt of mevinolinic acid as the starting material. U.S. Pat. No. 5,763,653 which describes the synthesis of simvastatin from the lovastatin amide prepared by treating lovastatin or the salt of mevinolinic acid with primary amine like propyl amine. The resulting lova amide has a hydrogen in the amide nitrogen which reacts with Lithium amide base thereby necessitating the need for larger equivalent of the amide base. Furthermore, the hydrogen in the amide nitrogen can react with the methyl iodide and lithium amide base and thus lead to side reactions and thereby lowering the overall yield.

These processes suffers from the fact that a primary amine is used for the ring opening and hence requires additional equivalent of the amide base reagent and suffers from other side reactions.

Accordingly the objects of the present invention is to overcome the aforesaid drawbacks by increasing the overall yield and the purity of the product and also to avoid the protection-deprotection of the hydroxy groups obtained from the lactone ring opening using highly expensive silyl or other protecting agents.

Another object of the invention is to minimize the cost of production of simvastatin by utilizing cheap raw materials and cost effective route for synthesis.

To achieve the said objective, the present invention relates to a process of manufacturing Simvastatin of formula IIa from Lovastatin characterized by the following steps:

step 1—converting Lovastatin to Lovastatin amide by treating Lovastatin with a secondary amine in an organic solvent, step 2—reacting the said lovastatin amide with metal amide base in tetrahydrofuran (THF) followed by treatment with alkyl halide and cooling the said mixture at a temperature ranging between −45° C. to −20° C. till C-methylated intermediate compound is formed, step 3—subjecting the said intermediate compound to hydrolysis to obtain its free acid, step 4—converting the said free acid to its ammonium salt and cyclizing the said ammonium salt to obtain simvastatin.

The organic solvent used is a polar or non-polar solvent and the alkyl halide is methyl iodide.

The mixture of lovastatin amide and metal amide base is cooled at −30° C.

The secondary amine is di-ethyl amine and the Lovastatin amide produced in step I is Lova-di-ethyl amide of formula IIIa wherein $R_1$ & $R_2$ are $C_2H_5$.

The secondary amine is pyrrolidine and the Lovastatin amide produced in step 1 is lova-pyrrolidine amide of formula Vb, wherein n=1.

The secondary amine is piperidine and the Lovastatin amide produced in step 1 is lova-piperidine amide of formula Vc, wherein n=2.

The metal amide base in THF used is prepared by adding n-butyl-lithium to pyrrolidine and cooling at a temperature ranging between −45° C. to −20° C.

The C-methylated intermediate compound formed in step 2 are of formulae IVa wherein $R_1 = R_2 = C_2H_5$; VIb wherein n=1 and VIc wherein n=2.

The novel intermediate compound of formula IIIa wherein $R_1$ & $R_2 = C_2H_5$ is N,N-Diethyl-7-[1,2,6,7,8,8a(R)-hexahydro-2(S), 6(R)-dimethyl-8(S)-[{2(S)-methylbutanoyl}oxy]-1(S)-napthyl]-3(R),5(R)-hydroxyheptanoic acid amide.

The novel intermediate compound of formula Vb wherein n=1 is N-Pyrrolidinyl7-[1,2,6,7,8,8a(R)-hexahydro-2(S),6(R)-dimethyl-8-[{2(S)-methylbutanoyl}oxy]-1(S)-napthyl]-3(R),5(R)-dihydroxyheptanoic acid amide.

The novel intermediate compound of structural formula IVa wherein $R_1=R_2=C_2H_5$ is N N,N-Diethyl7-[1,2,6,7,8,8a(R)-hexahydro-2(S),6(R)-dimethyl-8(S)-[2,2-dimethylbutanoyl}oxy]-1(S)-napthyl]-3(R),5(R)-dihydroxyheptanoic acid amide.

The novel intermediate compound of structural formula VIb wherein n=1 is N-Pyrollidinyl-7-[1,2,6,7,8,8a(R)-hexahydro-2(S),6(R)-dimethyl-8(S)-[2,2-dimethylbutanoyl}oxy]-1(S)-napthyl]-3(R),5(R)-dihydroxyheptanoic acid amide.

The novel intermediate compound of structural formula VIc wherein n=2 is N-Piperidinyl-7-[1,26,7,8,8a(R)-hexahydro-2(S),6(R)-dimethyl-8(S)-[2,2- dimethylbutanoyl}oxy]-1(S)-napthyl]-3(R),5(R)-dihydroxyheptanoic acid amide.

The instant process involves only 4 steps to synthesis simvastatin (IIa).

The intermediates (III and V) avoid the formation of other side reactions with the amide base and methyl halide.

Furthermore as the present invention utilizes a secondary amine, it results in a Lovastatin amide which does not contain any hydrogen in the amine nitrogen (III and V). Thus the Lovastatin amide (III and V) requires lesser equivalents of lithium amide base and thus increases the cost effectiveness of the route.

Also, the absence of the hydrogen in the amide nitrogen prevents side reactions and thereby resulting in purer products.

Additionally, because of the higher purity of the intermediate products, the downstream processing requires fewer purification steps, thus increasing the overall yield.

DETAILED DESCRIPTION OF THE INVENTION

According to this invention lovastation (Ia) is reacted with a diamine (secondary amine). The amine of choice is diethylamine and the intermediate obtained is the lova diethyl amide (III), wherein $R_1$ and $R_2$ is $C_2H_5$. Alternatively piperidine gives the lova piperidine amide (Vc) wherein n=2 and pyrrolidine gives lova pyrrolidine amide (Vb), wherein n=1.

The amide thus prepared is dissolved in dry tetrahydrofuran and cooled to −45° C. to −20° C. The metal amide base is prepared by adding n-BuLi to pyrrolidine and is cooled to −45° C. to −20° C. After about 1 hour, the alkyl halide, methyl iodide, is added and the contents are stirred for 30 min. Water is added to the reaction mixture and the layers obtained are separated. The organic layer is washed with brine solution and concentrated under reduced pressure to give an oily residue, which contains the intermediate (IVa or VIa). The crude intermediate is then hydrolyzed to give the free acid which is converted to the ammonium salt and is cyclized to give the final product, simvastatin.

The present invention is explained with the help of schemes I and II and examples.

EXAMPLE 1

Preparation of Simvastatin (IIa) from Lovastatin using Diethyl Amine

Step 1

N,N-Diethyl-7-[1,2,6,7,8,8a(R)-hexahydro-2(S), 6(R)-dimethyl-8(S)-[{2(S)-methylbutanoyl}oxy]-1(S)-napthyl]-3(R)-dihydroxyheptanoic acid amide (IIIa) Lovastatin (8.47 g) was dissolved in toluene (85 mL) and diethylamine (15 mL) was added. The mixture was heated to 90° C. and was refluxed for 36 h. The solution was cooled to 25° C. and kept at 25° C. for 4 h. The crystallized product was filtered and washed with toluene followed by hexane to afford the amide in a very pure form.

Step II

A solution of pyrrolidine (7.8 mL) and tetrahydrofuran (25 mL) was cooled to −30° C. A solution of n-butyl lithium (64 mL 1.4 M) was added keeping the temperature below −20° C. (18 15 min). After the addition is complete, the mixture was aged at −25° C. for 30 minutes. A solution of the amide (10 g) in THF (200 mL) was made and charged to the lithium pyrrolidide at −25° C. After the addition is complete, the mixture was agitated for 3 hours at −25° C. Methyl iodide solution was added (3.9 mL) in one portion and the agitation was continued for a further 30 min at −30° C. The mixture was quenched with water and rapidly agitated for 10 min. The phase was separated and the lower phase was re-extracted with hexane. The combined organic phase was washed with HCl (1 N) and 5% bisulfite syrup, which was used for the next step without any further purification.

Step III

The syrup so obtained was dissolved in ethanol (20 mL) at 25° C. and a solution of NaOH (3.15 g in 20 mL of water) was charged. The resulting solution was refluxed and after 3.5 hours, the mixture was cooled to 50° C. and ethanol was distilled under reduced pressure. The mixture was diluted with water and extracted with ethyl acetate: The combined ethyl acetate layers were back washed with 2% NaOH solution and the organic layer was discarded. The pooled aqueous layer was cooled to 10° C. and carefully acidified with 1.5 N HCl to pH=4 in the presence of ethyl acetate. The aqueous layer was re-extracted with ethyl acetate and the combined organic layer was washed with water to neutral pH. To the organic layer 3 mL of methanol was added and cooled to 10° C. $NH_3$ gas was bubbled until the precipitation was complete. The mixture was stirred for 30 min at 10° C. and filtered. The solid was washed with 5 mL of acetone and the product was dried to get the crude product.

Purification

The crude product was suspended in water and ethyl acetate was added. The mixture was cooled to 10° C. and acidified to pH=4 with 1.5 N HCl. The layers were separated and the aqueous layer was re-extracted with ethyl acetate. The combined organic layer was diluted with methanol and the temperature was brought to 20–23° C. A solution of ammonium hydroxide was added slowly. The mixture was stirred for 1 hour to get complete precipitation and filtered. The precipitate was washed with ethyl acetate and dried to afford the pure product.

Step IV

The purified ammonium salt was dissolved in 150 mL of toluene and heated to 100° C. under constant sweep of nitrogen for 6 hours. The solution was cooled to 25° C. and 2.5 g of activated charcoal and 2.5 g of neutral active alumina was added. The mixture was agitated for 30 min. and filtered through celite. The celite pad was washed with toluene (25 mL). The filtrate was concentrated under reduced pressure to afford a syrup. The syrup was diluted with ethyl acetate and 100 ml of petroleum ether (boiling range 60° C. to 80° C.) was added. The solution was left for aging for 30 min at 23–25° C. The precipitate obtained was filtered and the solid was washed with petroleum ether and dried at 40° C. for 2 hours to get the product, simvastatin.

Purification

The crude product, (4 g) was dissolved in methanol (40 mL) and 1.5 g of activated charcoal was added and stirred for 30 min. the mixture was filtered through a celite pad and the celite pad was washed with methanol. To the filtrate water was added slowly till crystallization sets in. The contents were stirred for 0.5 h and water (48mL). The contents were stirred for 1 h and cooled to 15° C. The precipitate was filtered and the solid was washed with 20% aqueous methanol (10 mL). The solid obtained was dried at 50° C. for 4 hours under vacuum to afford the pure title product.

The simvastatin obtained was of pharmaceutical grade.

EXAMPLE 2

Preparation of Simvastatin (IIa) from Lovastatin using Piperdine

Step I

N-Piperdiniyl-7-[1,2,6,7,8,8a(R)-hexahydro-2(S),6(R)-dimethyl-8(S)[{2(S)-methylbutanoyl}oxy]-1(S)-napthyl]-3(R),5(R)-dihydroxyheptanoic acid amide. (Vc)

Lovastatin (10 g) was dissolved in piperdine (75 mL) and refluxed. After 5 hours excess piperdine was removed under vacuum and purified by column chromatography using 60–120 silica gel to give the pure amide (Vc).

The intermediate (Vc) was converted to simvastatin by carrying out the reactions as described in example I by replacing with piperdine amide in the place of diethyl amide.

EXAMPLE 3

Preparation of Simvastatin (IIa) from Lovastatin using Pyrrolidone

Step I

N-pyrrolidinyl-7-[1,2,6,7,8,8a(R)-hexahydro-2(S),6(R)-dimethyl-8-[{2(S)-methylbutanoyl}oxy]-1(S)-napthyl]-3(R),5(R)-dihydroyheptanoic acid amide (Vb)

Lovastatin (10 g) and pyrrolidone (50 mL) mixture was heated to 70° C. for 6 hours. this mixture was concentrated to give a syrup and chloroform was added. The extract was concentrated under reduced pressure to afford the amide (Vb).

The intermediate (Vb) was converted to simvastatin by carrying out the reactions as described in example I by replacing with pyrrolidine amide in the place of diethyl amide.

While the invention has been described by reference to specific embodiments, this was for the purpose of illustration only. Numerous alternative embodiments will be apparent to those skilled in the art and are considered within the scope of these claims.

Ia

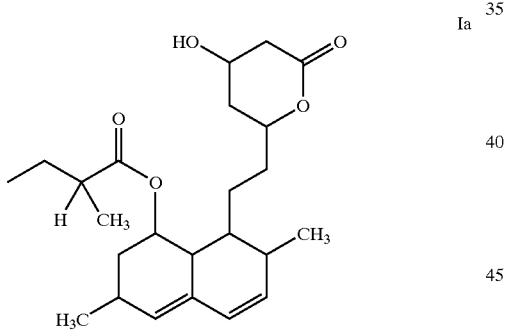

IIa

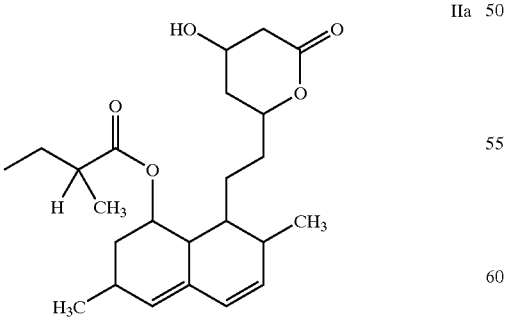

IIIa

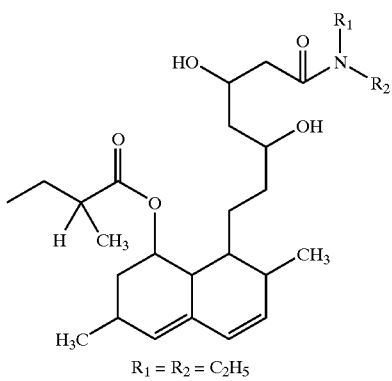

$R_1 = R_2 = C_2H_5$

IVa

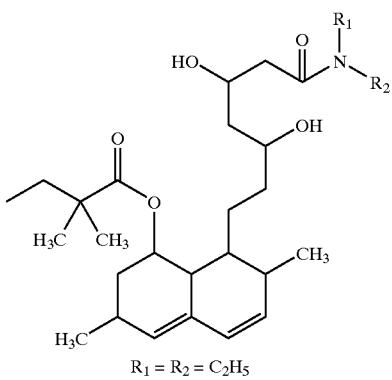

$R_1 = R_2 = C_2H_5$

Vb

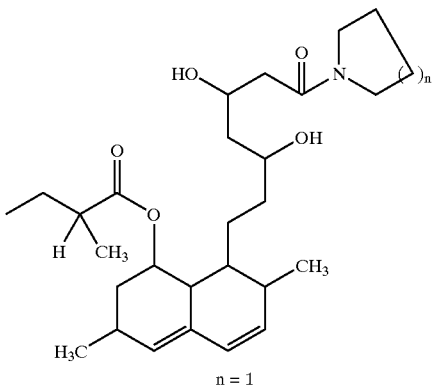

n = 1

VIb

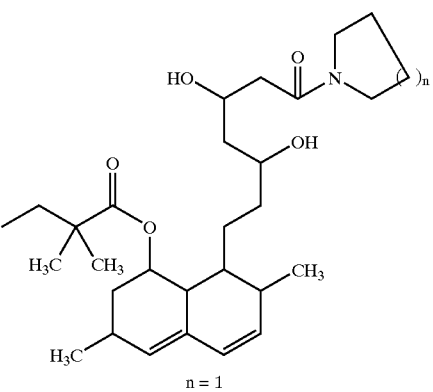

n = 1

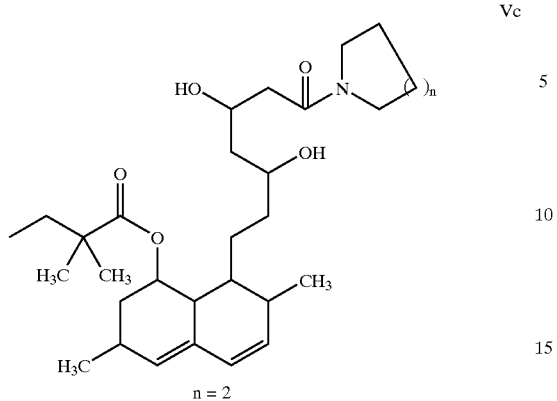
Vc
n = 2
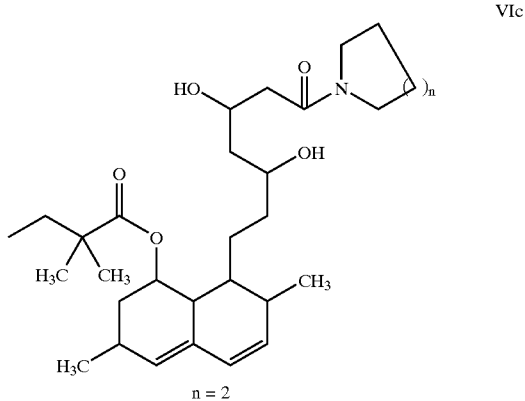
VIc
n = 2
Scheme I
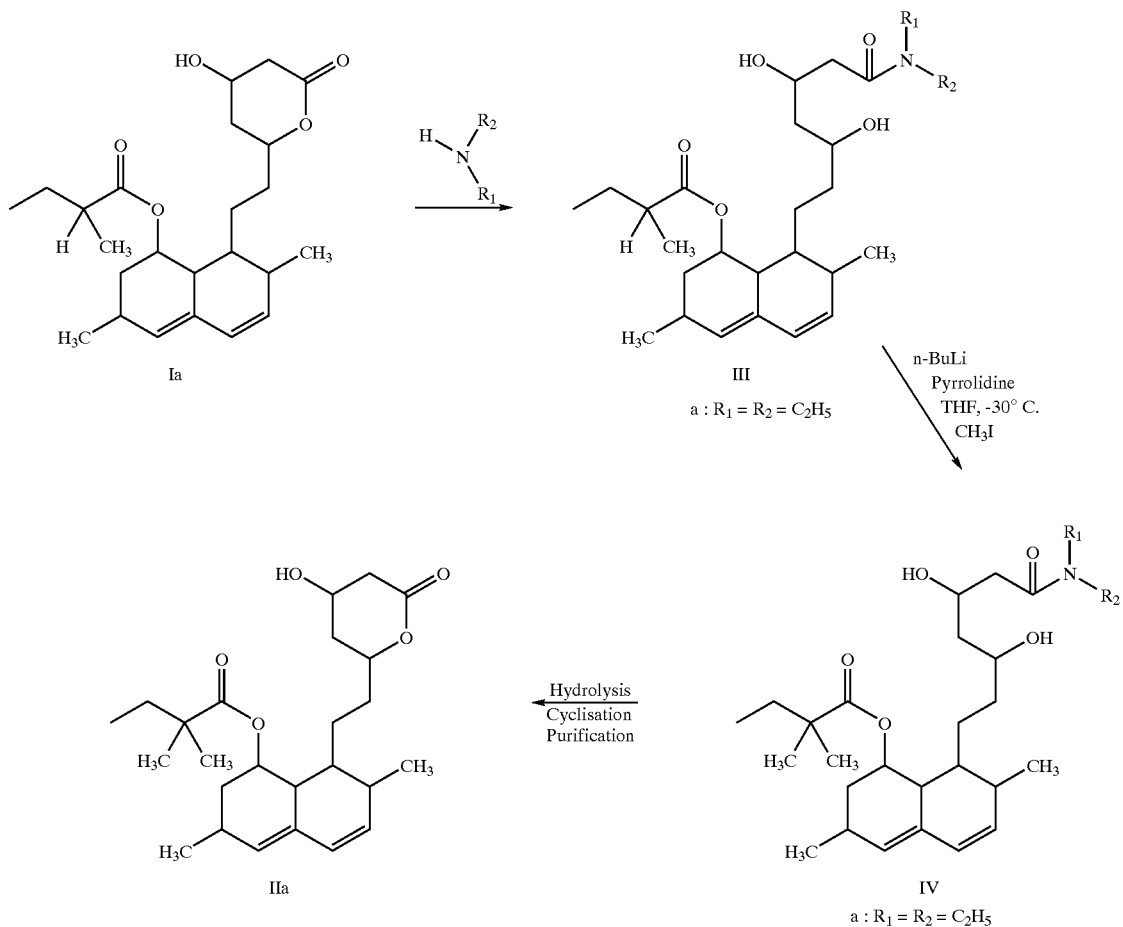

Scheme - II
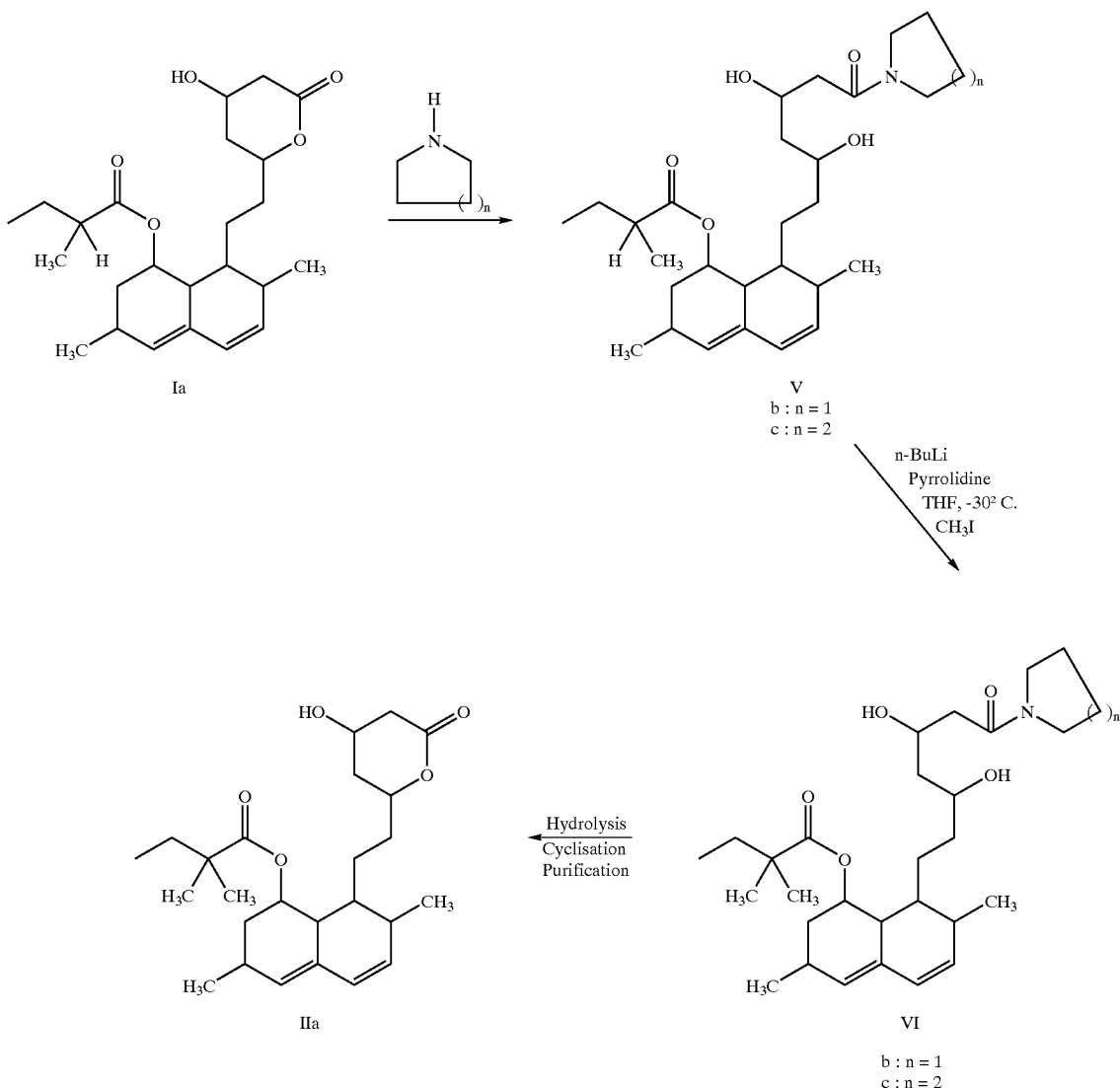
We claim:
1. A process of manufacturing Simvastatin of formula IIa:
the process comprising steps of:
step 1—converting Lovastatin of formula Ia:
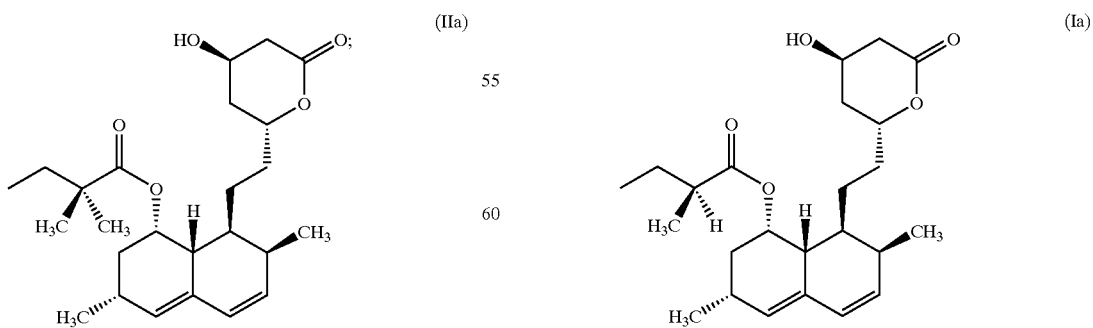

into a Lovastatin amide of formula III or V:

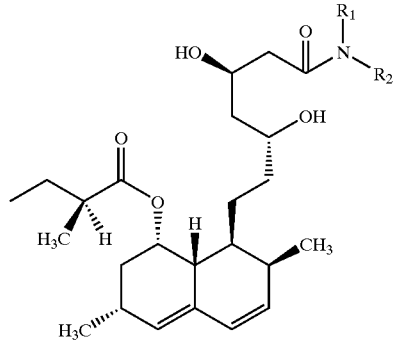
(III)

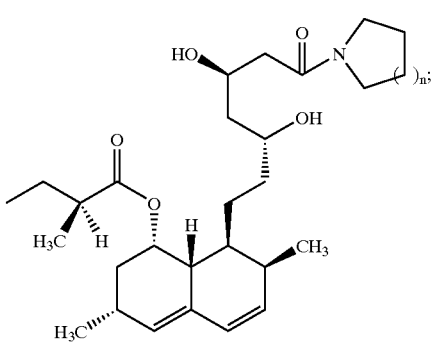
(V)

wherein $R_1$ and $R_2$ are independently alkyl and n is 1 or 2;

by treating Lovastatin (Ia) with a secondary amine in an organic solvent;

step 2—reacting the lovastatin amide of formula III or V with a metal amide base in tetrahydrofuran (THF) followed by treatment with an alkyl halide and cooling the said mixture at a temperature ranging between −45° C. to −20° C. until a C-methylated intermediate compound of formula IV or VI is formed:

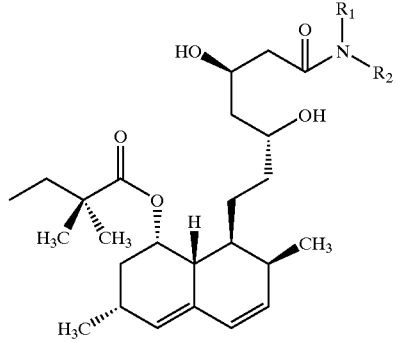
(IV)

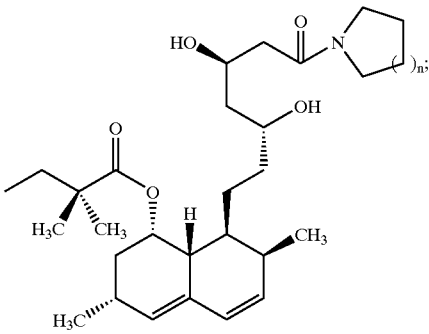
(VI)

step 3—subjecting the intermediate compound of formula IV or VI to hydrolysis to obtain the corresponding free acid; and step 4—converting the free acid to the corresponding ammonium salt and cyclizing the ammonium salt to obtain simvastatin (IIa).

2. The process of claim 1 characterized in that said organic solvent is a polar or non-polar solvent.

3. The process of claim 1 characterized in that said alkyl halide is methyl iodide.

4. The process of claim 1 characterized in that the mixture of lovastatin amide of formula III or V and metal amide base is cooled at −30° C.:

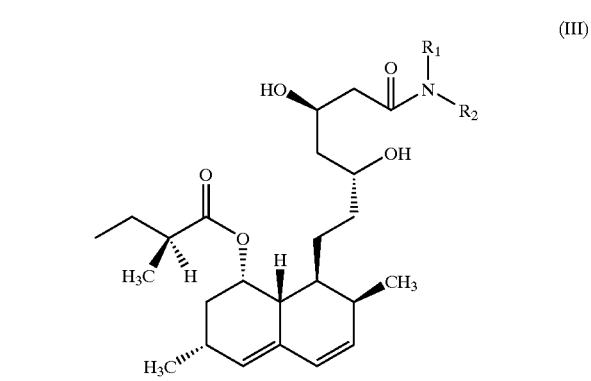
(III)

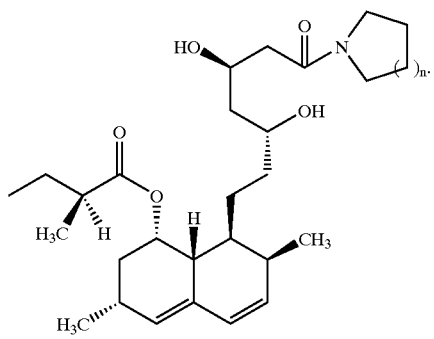
(V)

5. The process of claim 1 characterized in that said secondary amine is di-ethyl amine, $R_1$ and $R_2$ are each ethyl and the Lovastatin amide produced in step 1 is Lova-di-ethyl amide of formula IIIa:

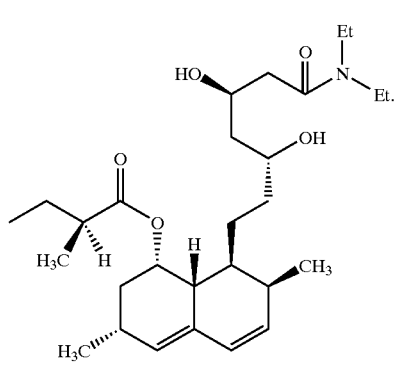

(IIIa)

6. The process of claim 1 characterized in that said secondary amine is pyrrolidine, n is 1 and the Lovastatin amide produced in step 1 is lova-pyrrolidine amide of formula Vb:

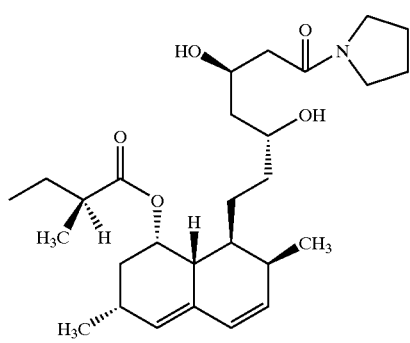

(Vb)

7. The process of claim 1 characterized in that said secondary amine is piperidine, n is 2 and the Lovastatin amide produced in step 1 is lova-piperidine amide of formula Vc:

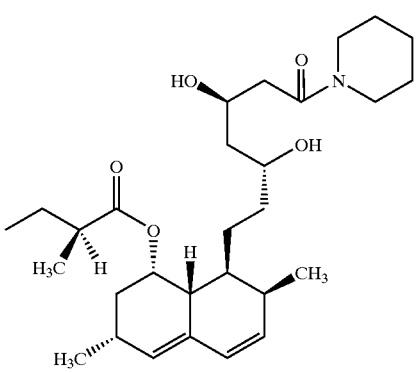

(Vc)

8. The process of claim 1 characterized in that said metal amide base in THF is prepared by adding n-butyl-lithium to pyrrolidine and cooling at a temperature ranging between −45° C. to −20° C.

9. The process of claim 1 wherein $R_1$ and $R_2$ are each ethyl and the C-methylated intermediate compound formed in step 2 is of formula IVa:

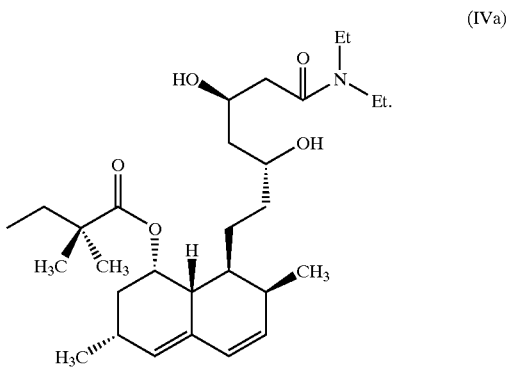

(IVa)

10. The process of claim 1 wherein n is 1 and the C-methylated intermediate compound formed in step 2 is of formula VIb:

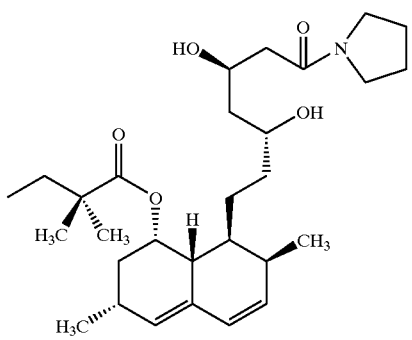

(VIb)

11. The process of claim 1 wherein n is 2 and the C-methylated intermediate compound formed in step 2 is of formula VIc:

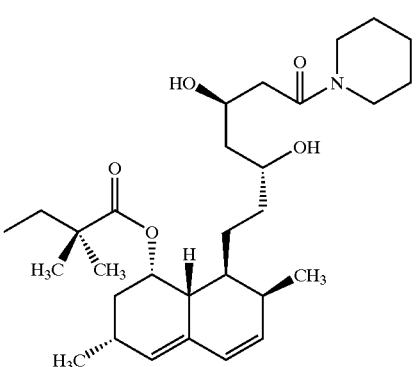

(VIc)

* * * * *